(12) United States Patent
Wyatt et al.

(10) Patent No.: US 11,300,503 B2
(45) Date of Patent: Apr. 12, 2022

(54) CARBON LADDER CALIBRATION

(71) Applicant: MLS ACQ, Inc., East Windsor, CT (US)

(72) Inventors: Eddie Dean Wyatt, Havertown, PA (US); Martin L. Spartz, Ellington, CT (US)

(73) Assignee: MLS Acq, Inc., East Windsor, CT (US)

( * ) Notice: Subject to any disclaimer, the term of this patent is extended or adjusted under 35 U.S.C. 154(b) by 521 days.

(21) Appl. No.: 16/113,856

(22) Filed: Aug. 27, 2018

(65) Prior Publication Data
US 2019/0064131 A1 Feb. 28, 2019

Related U.S. Application Data

(60) Provisional application No. 62/551,936, filed on Aug. 30, 2017, provisional application No. 62/551,933, filed on Aug. 30, 2017.

(51) Int. Cl.
| | |
|---|---|
| *G01N 21/3504* | (2014.01) |
| *G01N 30/02* | (2006.01) |
| *G01N 30/86* | (2006.01) |
| *G01N 33/00* | (2006.01) |
| *G01N 21/35* | (2014.01) |
| *G01N 30/04* | (2006.01) |
| *G01N 30/72* | (2006.01) |

(52) U.S. Cl.
CPC ......... *G01N 21/3504* (2013.01); *G01N 30/02* (2013.01); *G01N 30/8668* (2013.01); *G01N 30/8672* (2013.01); *G01N 30/7206* (2013.01); *G01N 33/0047* (2013.01); *G01N 2021/3595* (2013.01); *G01N 2030/025* (2013.01); *G01N 2030/042* (2013.01)

(58) Field of Classification Search
CPC .............. G01J 3/42; G01N 2021/3595; G01N 2030/008; G01N 2030/025; G01N 2030/743; G01N 21/031; G01N 21/33; G01N 21/3504; G01N 21/3581; G01N 21/359; G01N 21/64; G01N 21/65; G01N 30/74; G01N 30/8606; G01N 30/8641
See application file for complete search history.

(56) References Cited

U.S. PATENT DOCUMENTS

| | | | | |
|---|---|---|---|---|
| 4,802,102 | A * | 1/1989 | Lacey | ............... G01N 30/8624 702/32 |
| 9,606,088 | B2 * | 3/2017 | Spartz | .................... G01N 30/74 |
| 9,812,306 | B2 | 11/2017 | Andersson et al. | |
| 10,656,128 | B2 | 5/2020 | Wyatt et al. | |

(Continued)

FOREIGN PATENT DOCUMENTS

| | | | | |
|---|---|---|---|---|
| EP | 2541585 A1 * | 1/2013 | .......... | H01J 49/0036 |
| JP | 63082346 A * | 4/1988 | .......... | G01N 21/552 |
| JP | 63082346 A * | 1/2013 | .......... | H01J 49/0036 |

*Primary Examiner* — Nimeshkumar D Patel
*Assistant Examiner* — Gedeon M Kidanu
(74) *Attorney, Agent, or Firm* — HoustonHogle LLP

(57) ABSTRACT

A GC sample carbon ladder is generated with the help of one or more of the following techniques: correction of solvent effects; fit analysis of the spectrum obtained for a target member of the carbon ladder and a reference spectrum; fit analysis of a sample carbon ladder in comparison with reference spectral features; constraints for proper order of elution; and/or inclusion of all members in a selected carbon ladder set.

15 Claims, 8 Drawing Sheets

(56) References Cited

U.S. PATENT DOCUMENTS

| | | | |
|---|---|---|---|
| 2011/0054804 A1* | 3/2011 | Pfaff | G01N 30/8637 |
| | | | 702/25 |
| 2014/0297201 A1* | 10/2014 | Knorr | H01J 49/0036 |
| | | | 702/28 |
| 2015/0260695 A1* | 9/2015 | Spartz | G01N 30/74 |
| | | | 250/339.01 |
| 2017/0122920 A1* | 5/2017 | Spartz | G01N 30/20 |
| 2017/0299559 A1* | 10/2017 | Wyatt | G01N 30/8631 |
| 2018/0045694 A1* | 2/2018 | Wyatt | B01D 53/025 |

* cited by examiner

CARBON LADDER CALIBRATION

RELATED APPLICATIONS

This application claims the benefit under 35 USC 119(e) of U.S. Provisional Application No. 62/551,933, filed on Aug. 30, 2017, and is related to U.S. Provisional Application No. 62/551,936, filed Aug. 30, 2017, both of which are incorporated herein by reference in their entirety.

BACKGROUND OF THE INVENTION

Gas chromatography (GC) is an analytical method that measures the content of various components in a sample. The method for separating chemical substances relies on differences in partitioning behavior between a flowing mobile phase as phase) and a stationary phase supported in a column to separate the components in a mixture. As the gas flow passes through the column, the sample components move at velocities that are influenced by the degree of interaction of each component with the stationary phase in the column. Consequently, the different components separate as the components elute from the column.

While GC can be used to resolve a mixture into its various components according to retention profiles of the different molecules passing through the GC column, and can potentially handle mixtures containing large numbers (hundreds, for instance) of substances, identifying the molecules that elute from the column is more problematic. For example, full peak separation is often needed to qualify and quantify compounds present. Small sample sizes and dynamic ranges, and the need for continuing calibration are additional drawbacks.

To address the need for rapid and sensitive identification of the molecular species present, GC has been integrated with techniques such as mass spectrometry (MS) or Fourier transform infrared (FTIR) spectrometry.

Gas chromatography-mass spectrometry (GC-MS) is probably the most widespread tandem technique in the analytical instrumentation industry today. GC-MS systems are versatile and are employed across many different industries, particularly for environmental, chemical, petroleum, pharmaceutical, and toxicological applications. While GC-MS is a fast, sensitive technique suitable for multiple component detection and spectral identification, capable of measuring atomic species and supported by large available spectral libraries, it suffers from some disadvantages. These include compound separation to prevent MS interferences, non-linear calibrations, poor precision and accuracy (requiring constant calibration) and limited dynamic range. Problems also are encountered when high concentrations are present that can allow for chemical ionization to occur, generating questionable data.

While GC-MS is the more commonly deployed solution, Gas Chromatography-Fourier Transform Infrared Spectrometry (GC-FTIR) provides a powerful analytical tool that is particularly useful to distinguish among structural isomers that have identical electron impact and chemical ionization mass spectra.

Nevertheless, historically the designs of GC-FTIR systems have been plagued with their own limitations. For example, many GC-FTIR sample cells utilize a "light pipe" (typically a cell or cuvette used for passing both gas eluted from the GC column, and light from the FTIR interferometer). The light pipe is made relatively short to prevent peak dilution through the IR cell and its eventual IR detection or secondary detection. Since IR absorption is proportional to cell path length, this short path length limits the sensitivity (minimum detection limit (MDL)) of the technique. Problems also arise in cases in which GC peaks come off very quickly. Since the light pipe has a relatively large volume when compared to the flow rates of the GC, the gas can become diluted, making measurements more difficult.

More recently, Spartz, et al., in U.S. Pat. Appl. Pub. No. US 2015-0260695 A1, now U.S. Pat. No. 9,606,088, issued Mar. 28, 2017 and in U.S. Pat. Appl. Pub. No. US 2017-0122920 A1, all of which are incorporated herein by this reference in their entirety, disclose GC-FTIR techniques and systems with the objective of coupling existing or newly developed approaches, such as GCs, and/or optical spectroscopy systems (e.g., FTIRs) in ways that reduce or minimize the deficiencies encountered with conventional arrangements.

SUMMARY OF THE INVENTION

The invention generally addresses the correlation between known GC retention indices and the corresponding retention times observed with a particular GC column. Many implementations described herein pertain to carbon ladder calibrations based on a combination of temporal separation and spectroscopic measurements. Even with a powerful approach such as that available with some GC-FTIR systems, some difficulties remain. They include, for example, problems related to solvent background, peak detection, and/or peak identification. In calibration work, these problems can have far reaching consequences.

Approaches for finding local maxima (peaks) on a data curve have existed. Nevertheless, knowing which peaks in the graph correspond to the compounds to be relied upon for calibration purposes and which correspond to the solvent used can present difficulties. Removal of the solvent features would facilitate identification, location, and assignment of the peaks observed.

Some peaks, however, may not be recoverable even after solvent effects are reduced or eliminated. Such results can be misleading, potentially leading to a data collection process that is cut short.

Therefore, a need exists for techniques that automatically find the peaks for a set of compounds selected for calibration purposes, a carbon ladder, for example. Specifically, a need exists for methods that can identify a peak observed on the chromatograph, matching it to the correct hydrocarbon. A need also exists for generating a carbon ladder chromatogram that represents a reliable calibration.

Aspects described herein relate to a method for calibrating retention times of a set of compounds typically for the purposes of calibration, a carbon ladder, for example, through a given gas chromatography column. For example, a sample containing a carbon ladder (a set of hydrocarbons that differ from one another by one carbon atom, for example) is passed through a GC column. Elution times are detected and recorded by optical spectroscopic means such as FTIR. The data can be corrected for solvent effects. Comparing the observed spectrum of one of the unassigned members of the carbon ladder, with a known (reference) spectrum of one or more members in the carbon ladder, over the same spectral region, can reveal the match or "fit" between the two. The goodness of the fit, expressed, for example, by the least error observed in this comparison can be used to assign or identify the unassigned compound as a specific member of the carbon ladder. The protocol can then be repeated to assign other members of in the carbon ladder and generate a potential calibration candidate. Some implementations introduce constraints to ensure that carbon ladder members elute in the proper sequence. Other constraints can be imposed to ensure that all members of the ladder set are included, thereby avoiding gaps. In some cases, missing members are allowed only at the beginning and/or the end of the ladder. Further, the protocol can be designed to relax the "no gap" constraint under prescribed situations.

A parameter such as the average error for the superimposed carbon ladder over the chromatograph peaks can be used to generate an aggregate metric for the hydrocarbon peak assignment. Other parameters that can be utilized include but are not limited to total error, goodness of fit, and so forth.

The target carbon ladder is then shifted, forward and backwards across the peaks, moving the entire ladder, one peak at the time, for example. An error metric is computed for each of the resulting arrangement. The ladder positioning presenting the least error is then selected as the calibrated carbon ladder chromatogram.

Thus, in one embodiment, the invention features a process for generating a carbon ladder calibration chromatogram. The process includes generating an initial chromatogram of a sample eluting through a GC column, wherein the sample comprises carbon ladder compounds; comparing the optical spectrum of one or more observed peaks in the initial chromatogram with reference optical spectra; assigning the one or more observed peaks by determining a best match between the optical spectrum of the one or more observed peak and the reference optical spectra to obtain a candidate calibration chromatograph; shifting the candidate calibration chromatogram by one or more carbon numbers to determine an overall best match, thereby generating the carbon ladder calibration chromatogram.

Practicing embodiments described herein can be used to calibrate retention times of a carbon ladder. The calibrated carbon ladder can then be used to estimate elution times on the instrument for other compounds, based on their elution indices, and eventually in the analysis of unknown components present in a sample. Processes described herein can be automated to a robust approach that increases the degree of confidence in the integrity of peak assignment, inclusion of all members in the carbon ladder and the resulting calibration.

In some aspects, solvent effects that can obscure spectral features normally used to identify members in the ladder are reduced, minimized and, in many cases, entirely eliminated. Techniques described herein facilitate proper identification of carbon ladder members. Ensuring that the proper elution order is maintained and that all members in a selected ladder set are, in fact, accounted for and thus the run is not terminated too early, yield calibrations of increased reliability. In some cases, the calibration process is streamlined since only those carbon numbers that have a reference spectrum need to be used for a successful assignment of peaks.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

Figure 1:
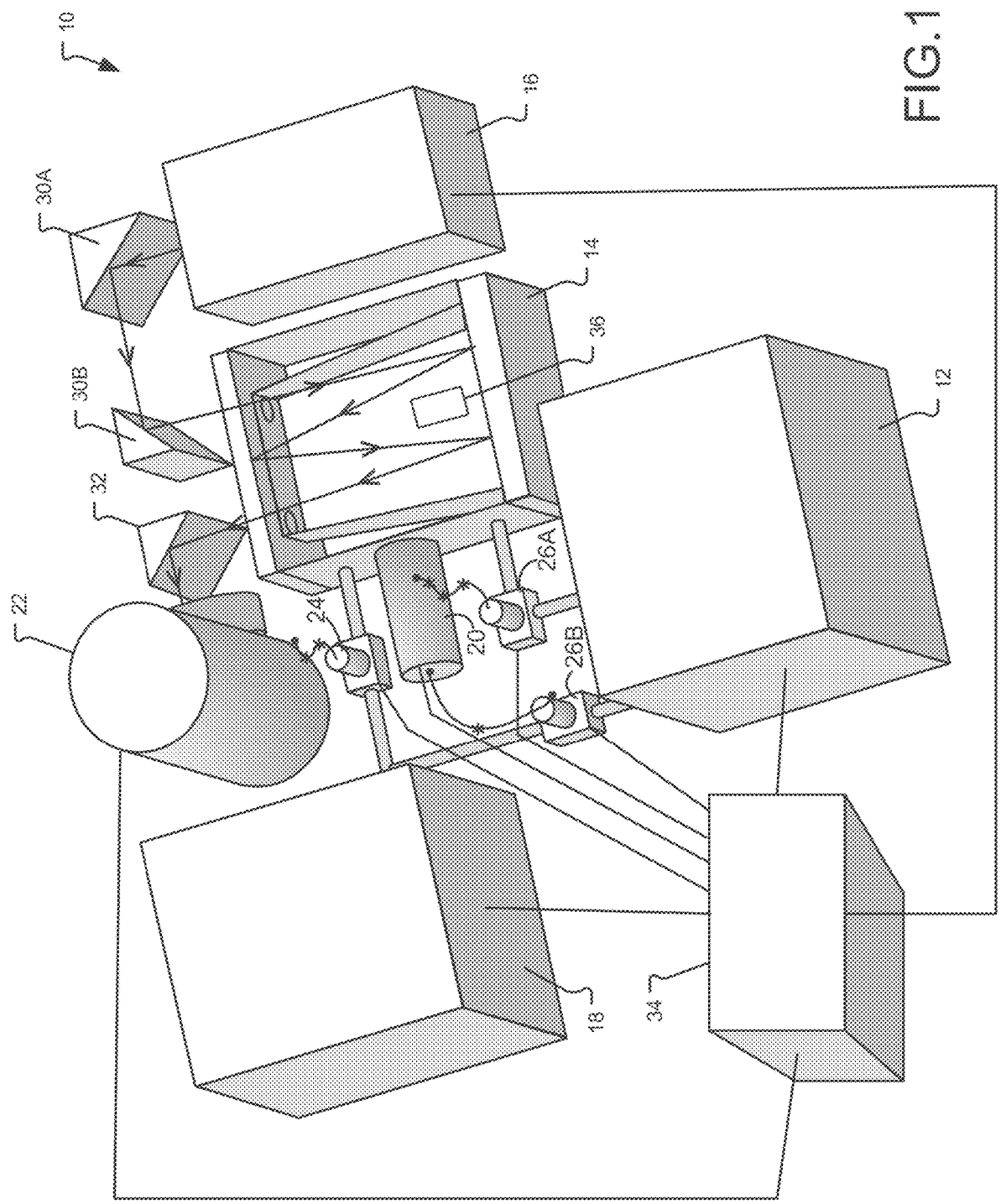
FIG. 1 is a schematic diagram of a sample analysis system, which is suitable for use with the process of the present invention.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Embodiments described herein generally relate to techniques that can be utilized in data analysis in GC-FTIR systems, and, in particular, the calibration of standards typically used in GC to the specific system being used. In many implementations, the task addressed is that of generating a system-dependent calibration chromatogram that provides a "template" of retention times for a series of related compounds with known retention indices, alkanes in a carbon ladder, for example.

Generally, the process disclosed is implemented by software executed by a computer. The process automatically analyzes spectra, e.g., absorption spectra, produced by a chemical analysis system, e.g., a GC-FTIR. (Gas Chromatography-Fourier Transform Infrared) system. A suitable system and method that couple a time-resolved separator, e.g., a gas chromatograph (GC), to an analyzer that relies on optical spectroscopic technology such as FTIR or other spectroscopy technology, is described in U.S. Pat. Appl. Pub. No. US 2015-0260695 A1, now U.S. Pat. No. 9,606, 088 and U.S. Pat. Appl. Pub. No. US 2017-0122920 A1, these patent documents being incorporated herein by this reference in their entirety.

Generally, the system in the U.S. Pat. No. 9,606,088 is configured for analyzing a sample, typically a mixture containing more than one distinct chemical species. Components in the sample can be separated through various suitable techniques. A common temporally resolving separator is a GC column in which compounds in a mixture become separated based on their flow rates. Typically, lighter gases will elute through a column quicker than heavier ones. In a sample analysis system such as, for example, that described in U.S. Pat. No. 9,606,088, the GC column allows the FTIR system to differentiate substances with similar looking spectra using time. The electromagnetic-based radiation spectroscopic device (an FTIR system, for example) can be used to identify and, in many cases, quantify the species present, resolved temporally by the separator. The coupling between separator and optical spectroscopic analyzer can be based on a sample cell having particular features. Controls, automation instrumentation, computer interfaces, algorithms and/or software-related features also can be provided.

Shown in FIG. 1, for example, is a system 10, including a separator such as gas chromatograph (GC) 12, sample cell 14, and a spectrometer, e.g., FTIR spectrometer 16, which includes a light, and more generally, an electromagnetic (EM) radiation source. In specific implementations, GC 12 and/or FTIR spectrometer 16 are commercially available instruments, with exhaust from the GC being often directly coupled to the FTIR sample cell.

Other embodiments described herein can be practiced or adapted to other separator systems and/and other spectrometry beyond GC-FTIR. For instance, the spectrometry system can determine the spectral response of the components in the sample cell in one or more of the following spectral regions millimeter, microwave, terahertz, infrared (including near-, mid- and/or far-infrared), visible, ultraviolet (UV) (including vacuum ultraviolet (VUV)), x-rays and/or gamma. Further, the detection employed can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra of the components in the sample cell 14.

In general, the GC uses a stationary phase, which is typically a microscopic layer of liquid or polymer on an inert solid glass or metal tube, i.e., a column. The mobile phase is a carrier gas, usually an inert gas such as helium or a non-reactive gas such as nitrogen. The carrier gas flow is controlled by flow controllers and/or a series of valves to maintain or vary the flow rate during the separation. The flow controllers and valves can also be used to allow the entire sample or a fraction of the sample to enter the column. The column is located in an oven where the temperature of the gas passing through the column can be controlled. The gaseous compounds interact with the walls of the column or stationary phase, causing each compound to elute at a different time, known as the retention time of the compound.

Carrier gases that can be used include nitrogen ($N_2$), for instance ultra-high purity (UHP) $N_2$, or another suitable gas or gas mixture as known in the art.

Typically, output from the separator such as GC 12, is in a gaseous state, containing one or more gases and/or vapors. This output is directed to sample (also referred to as gas) cell 14.

In some examples, the cell 14 is a vessel that can be evacuated and configured to maintain a gas pressure lower than the surrounding (atmospheric or ambient) pressure to integrate the sample over time. In specific implementations, the pressure in the sample cell is within the range of about 0.001 to about 1.0 atm. For instance, a flow rate of 1 mL/minute, a sample cell volume of 200 mL and a starting gas cell pressure of ½ atmosphere can provide a 100 minute time period for data acquisition. This is considered to be a sufficient time window for most GC sample analyses. The pressure in the sample cell is reduced with a vacuum pump 18, or alternative apparatus capable of drawing a vacuum. The pressure in the sample cell can be monitored with a sensor, such as an absolute pressure sensor 20.

In other examples, the cell 14 is a partially integrating cell a flow cell, such as a light pipe, through which the output from the separator flows.

In some cases, no vacuum is required and the system can be operated at a suitable pressure. For instance, a compressor or column head pressure could be used to compress or flow the output from the GC into and possibly through the sample cell 14. Preferably, over pressurizing is avoided.

Sample cell 14 also receives electromagnetic radiation, for instance from light generated in FTIR arrangement 16 and can be designed to fit in the sample compartment of a commercial FTIR or other type of spectrometer. The cell is provided with optical components, such as windows that allow transmission of an electromagnetic radiation beam within a desired wavelength (or frequency) range into and out of the cell 14.

In the specific illustrated example, output radiation exits sample cell 14 and is directed by reflector 32 to detector 22, for instance a MCT (mercury cadmium telleride) device suitable for measuring the light in an FTIR. Specific examples employ liquid nitrogen cooled MCTs. One example of a suitable detector for a broad spectral analysis capability can be a 1 mm mid-band MCT with a cutoff of 16 μm.

System 10 includes electronics and computer systems 34. It further includes a video displays or computer display device. Further, other devices, units, interfaces, data co-processors, and/or other components for data processing, analysis (including multivariate qualitative and quantitative), recording, reporting, equipment controls, automation, flow control and controllers, pressure sensors and controllers, heaters and temperature controllers, valves and vacuum generation technology, spectral libraries, and so forth are included. These components are generally also indicated by reference numeral 34. One or more processors, memory devices, and so on, are provided in the computer system 34 for executing processes of the present invention.

During operation, gas is captured or resident in sample cell 14 for a specific time, based on the gas turnover rate in the sample cell. Various flow conditions can be employed. In a transient mode, for instance, the entire experiment (run) is conducted under a set, i.e., unchanging pressure, e.g., under a set vacuum pressure. In a full integration mode, sample cell 14 is evacuated and the sample is allowed to accumulate in the sample cell, with the pressure changing throughout the analysis. Also possible is a partial integration mode, where the sample cell is evacuated to a set pressure and a dilution gas is added and maintained in the cell for a period of time, e.g., 1 minute. Other operating modes can be employed, such as, for example, a mode that reduces the size of the data set. In other cases, a flow cell, such as a light pipe, is employed. In the light pipe or similar flow cell, the gas continuously flows through the cell with a characteristic residence time in the cell.

In some arrangements, a continuous carrier gas flow (e.g., $N_2$ or other suitable carrier gas) directed from GC 12, into the sample cell. If desired, sample cell 14 can be closed to the $N_2$ flow from GC 12, for a given time interval. In yet other arrangements, the carrier gas, or the sample from the GC can be diverted to a secondary pumping service (not shown in FIG. 1) to prevent spectral interference from large concentration compounds such as solvent species. The flow can then be switched for sample collection. If pumping continues, the compounds that come off during this time will be standard chromatographic components (peaks) and their concentrations can be calculated as such. The peak will go up and go down as it enters and exits the sample cell so no further averaging will be done.

If sample cell 14 is initially evacuated, then sealed from pump 18, the carrier gas and sample components from the GC can accumulate in or flow through the sample cell and spectra can be obtained during the entire data collection. Since the chemicals are captured in the sample cell, the entire amount of each gas (compound) can be measured once it has completely eluted from the separation device (GC). Since the gas cell is a multiple pass gas cell in a preferred embodiment, there can be an increased absorption for each gas when compared to "light pipe" system in an optimized design. By letting all the gas remain in the gas cell, this in effect integrates the sample peak from a traditional analyzer where the sample moves past or through the detection system. This integration provides a further enhancement in SNR, which can be a factor of 2 to 5 times since the entire amount of sample is measured once it has completely eluted. Typically, this improvement is dependent on the width of the eluted peak.

In specific implementations, a control circuit managed by the computer system 34 dynamically controls the sample cell pressure. For instance, automated valves can be set to pull a vacuum on sample cell 14 before starting a run or drawing the components through a flow cell. Pressure levels in the cell can also be controlled automatically. In many cases, isolating sample cell 14 from pump 18, thus allowing gas to accumulate in the sample cell, is also performed automatically. Automation can be used to set a desired carrier gas flow from the separator, e.g., GC 12, into the sample cell, to isolate the cell from the carrier gas, to divert the carrier gas to any secondary pumping station, to switch the flow to the FTIR gas cell for sample collection, and so forth.

With respect to data handling such as data collection and analysis, a process carried out in a system such as system 10 of FIG. 1 can involve data collection; data integral, differentiation or signal averaging; data spectral deconvolution/quantification; data reporting; among others. Computed data, plots generated by computer system 34, for instance, are displayed in a graphical user interface of the display device of the computer system 34.

During operation, a sample is directed from the temporally-resolving separator to the sample cell, e.g., a gas cell that fully or partially integrates the components provided by the separator. The sample cell can be partially or fully evacuated and fluids such as gases and/or vapors are allowed to accumulate in the sample cell, effectively integrating their spectral signatures. Multiple spectra obtained over a time interval could then be averaged to best measure the integrated concentration in the sample cell. Obtaining a moving background that includes spectra from a previously eluted sample component, e.g., previously eluted chemical species, allows for the analysis of the current eluting components without interference from previously eluted components. The integrated and averaged multiple spectra can be corrected by using a similarly collected moving background, and the corrected data are compared to known spectra to identify one or more components, e.g., chemical species such as atoms, molecules, molecular fragments, ions, present in the sample component.

Data integral/differentiation/signal averaging functions employed by the computer system 34 can utilize, for instance, a 1 minute moving spectral average. Time spacing between background and sample spectrum can be varied. Data spectral deconvolution/quantification can be provided by a moving multiple linear regression based on compound retention index. A new regression matrix can be built for each spectrum analyzed in real time by the computer system 34. Compounds selected for each regression are present for a relative distance +/− of its own retention index. Very high concentration components, internal standards or solvents can be present in a select set or in all regressions.

Typically, calibration data can be provided for each compound, and, in specific implementations at multiple concentrations. Retention index per compound can be determined using hydrocarbon reference standards or obtained from current mass spectral library data and employed by the computer system 34. For instance, retention index data are available from many sources, as known in the art, and are typically provided based on the type of column being utilized. Calibration data can be called when a certain index is reached, e.g., for the deconvolution operation. An initial prediction could be performed to determine which compounds within a retention index window might actually be present. This initial screening will limit the number of compounds then utilized in the multivariate analysis.

Further design and operation details can be found in the above-mentioned references (U.S. Pat. Appl. Pub. No. US 2015-0260695 A1, now U.S. Pat. No. 9,606,088). Calibration techniques that can be utilized in a system such as this (or other GC-FTIR instruments) are further described below. A computer system, e.g., computer 34 in FIG. 1, and/or any associated components are configured for executing software for implementing embodiments of the present invention, allowing automated data handling and analysis based on processes described below.

As seen above and known in the art, compounds in a mixture can be separated by GC according to their flow rates through a column. The time needed by a given compound to pass through (elute) depends not only on the intrinsic nature of the compound (lighter vapors generally elute faster than heavier ones, for instance) but also on external factors such as properties of the column (length, diameter, coating-related parameters, and so forth), carrier gas velocity, pressure, temperature, and so forth.

Since these and/or other variables are found to affect absolute retention times, GC analysis typically utilizes relative retention parameters, generally based on comparing the retention time of an unknown substance to that of a (known) standard compound. Expressing retention parameters in relative terms cancels out many operational effects such as, for example, column dimensions or carrier gas flow rates. Thus using the "retention index" of a certain organic compound, can normalize its retention time to the retention times of adjacently eluting compounds, in many cases adjacently eluting hydrocarbons, e.g., n-alkanes ($C_nH_{2n+2}$), and allows comparing values measured by different analytical laboratories under varying conditions. To illustrate, if pentane has a retention index of 500 and hexane a retention index of 600, isopropanol, with a retention index of 574, is expected to elute through the column between the times when pentane and hexane elute, after pentane and before hexane.

Mathematical relationships for determining retention indices have been developed for isothermal as well as temperature programmed CG and are known in the art. In the case of isothermal and nonisothermal (temperature programmed) GC, the Kovats retention index of an unknown compound, $I_x$, is given, respectively, by relationships (I) and (II) below:

$$I_x = 100_n + 100[\log(t_x) - \log(t_n)]/[\log(t_{n+1}) - \log(t_n)] \quad (I)$$

$$I_x = 100_n + 100(t_x - t_n)/(t_{n+1} - t_n) \quad (II)$$

where $t_n$ and $t_{n+1}$ are retention times of the reference n-alkane hydrocarbons eluting immediately before and after chemical compound "X" and t is the retention time of unknown compound "X".

In the case of isothermal analysis, if a logarithm of adjusted retention times or relative retentions of n-alkanes is plotted with carbon numbers, they will show a linear relationship. For temperature programming analysis, the peaks of n-alkanes appear at even intervals and the retention index obtained is known as linear retention index (LRI).

By analogy to Kovats indices, Lee indices characterize a series of compounds including benzene, naphthalene, phenanthrene and others. Tables of retention indices are available to help identify components by comparing an experimentally found retention index with known values. A computer system, e.g., computer 34 in FIG. 1, can include or can be connected to one or more libraries or database(s) that provide retention indices for a wide variety of compounds.

To determine when a compound will elute in a particular system (e.g., a specific lab or field instrument) retention indices (of universal use) are converted to retention times, employing, for instance, a set of compounds, referred to herein as a "carbon ladder", with the goal of generating a system-dependent carbon ladder calibration.

The carbon ladder calibration is generated by running through the system, e.g., the system in FIG. 1, a known sample containing a set of hydrocarbon chains, e.g., alkanes such as pentane, hexane, heptane, octane, and so on. The hydrocarbons can be referred, respectively, as C5, C6, C7, C8, etc., depending on the number of carbon atoms in the chain. Lower and/or upper limits can be selected, as known in the art, based on experience, special circumstances, experimental determinations, and so on. In many cases, a suitable carbon ladder will include, for example, C5 through C15, C16, C17, C18 or higher.

Figure 2:
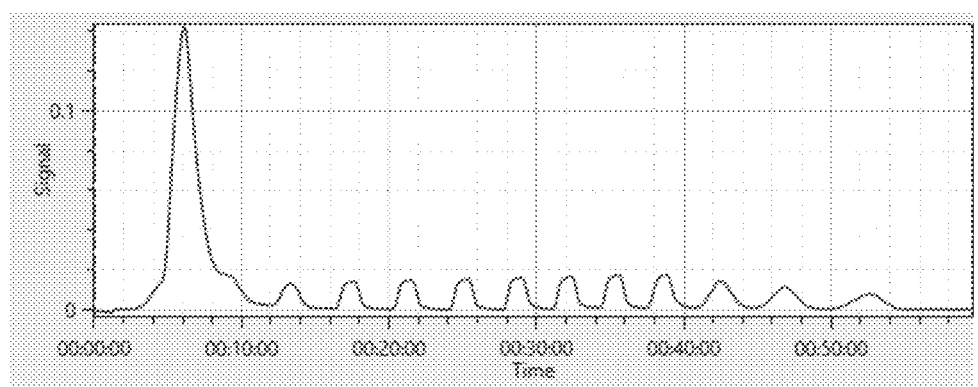
FIG. 2 is an illustrative carbon ladder chromatogram.

For an initial run of the carbon ladder through the GC column, the time when each of the hydrocarbon peaks is recorded (as measured by a suitable detection means) gives rise to a chromatogram (generally a graph of the peak absorption over time, as shown in the illustrative plot of FIG. 2). This is then used to convert retention indices into retention times. Thus, a chromatogram can be relied upon to identify when each hydrocarbon in the carbon ladder is peaking in a given system (associated with a given GC column) and hence to determine the retention time for each of the hydrocarbon in that system.

Linear interpolation techniques are employed for retention indices than lie between two known hydrocarbons. For example, if C5 (retention index of 500) is found to elute at 300 seconds and C6 (retention index 600) at 400 seconds, an unknown, also referred to herein as a "target" compound with a retention index of 550 is expected to elute half-way in between, with a retention time of 350 seconds.

In the GC-FTIR system 10, a chromatogram can be generated by selecting the maximum absorption value over a restricted wavenumber ($cm^{-1}$) range for each spectrum in the data set. For a carbon ladder set including alkanes, a suitable wave number range for detecting maximum absorption is the region between 2800 and 2960 $cm^{-1}$, corresponding to the typical alkane C—H stretch. Other frequency ranges can be selected.

Figure 3:
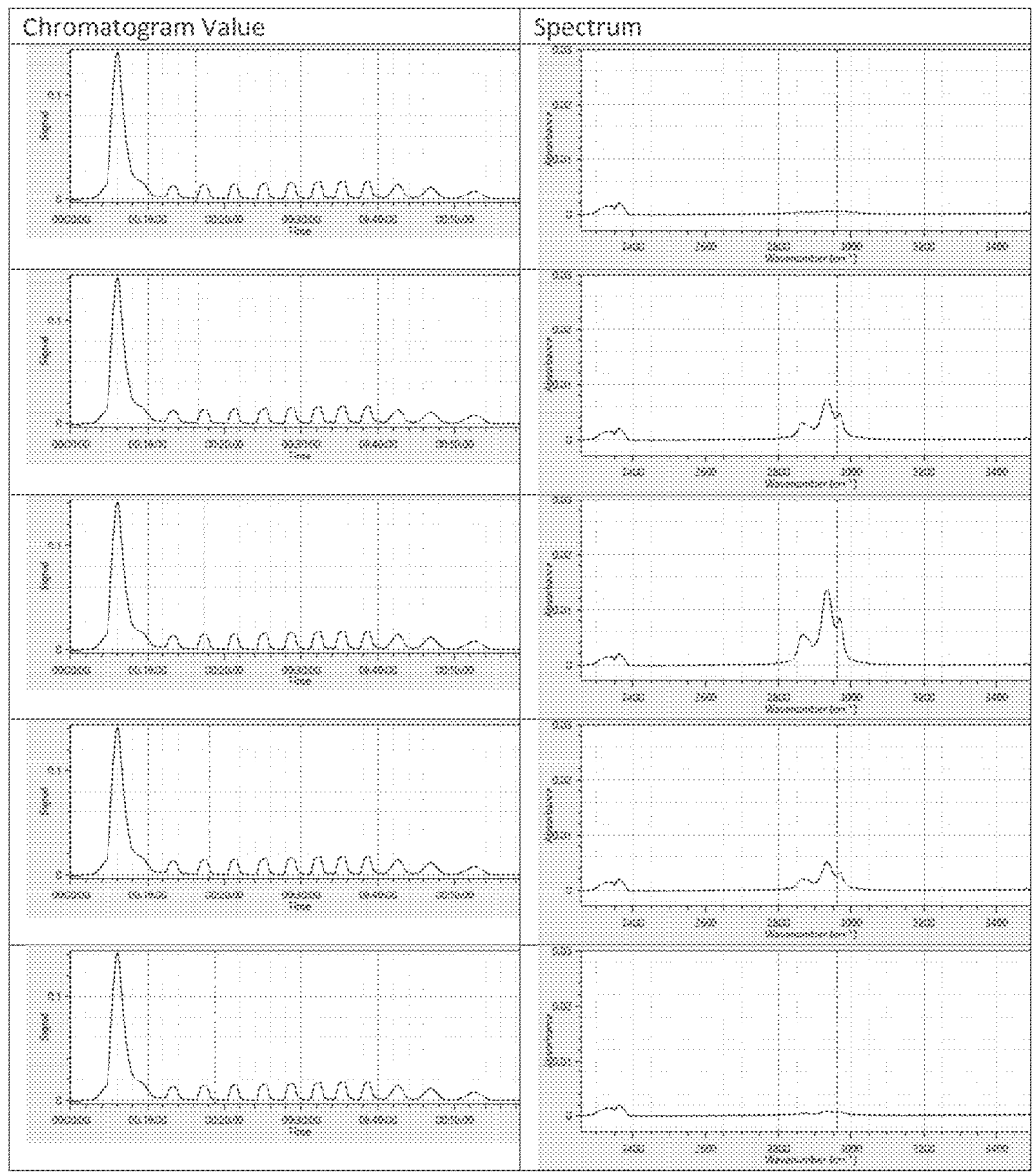
FIG. 3 depicts the correlation between the features observed by FTIR (spectral region between the vertical lines in the right-hand plots of absorbance as a function of wavenumber) and the time spanned between the vertical lines drawn in the left-hand chromatograms.

Shown in FIG. 3 is a correlation between the features observed by FTIR (spectral region between the vertical lines in the right-hand graphs) and the time spanned between the vertical lines drawn in the left-hand graphs. Thus, the maximum wavenumber in the region between the vertical lines on the right-hand spectrum graph is used to compute the peak absorption value between the vertical line on the left graph.

Some situations, however, can present assignment complications and/or other difficulties.

Figure 4:
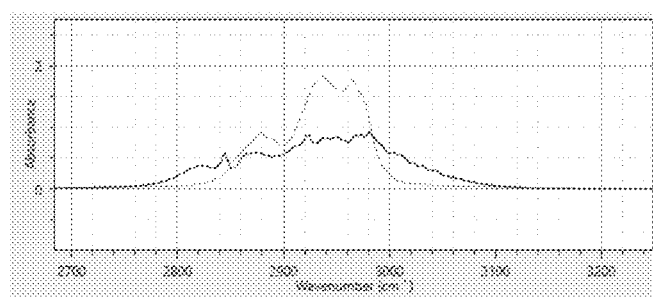
FIG. 4 is a plot of absorbance as a function of wavenumber showing the superposition of the hexane absorption (gray) and that of methanol (black) in the 2900 and 3000 $cm^{-1}$ spectral region.

For example, a solvent often used for the carbon ladder calibrations is methanol, a substance that presents spectral feature in the same range as the C—H region selected to compute chromatogram peaks. In FIG. 4, the gray curve corresponds to hexane spectral features, while the black curve to methanol absorption peaks. When methanol is present in high concentration (an occurrence often encountered, in particular at the onset of a run), it can completely obliterate or obscure spectral features identifying one or more hydrocarbons in the carbon ladder.

Figure 5:
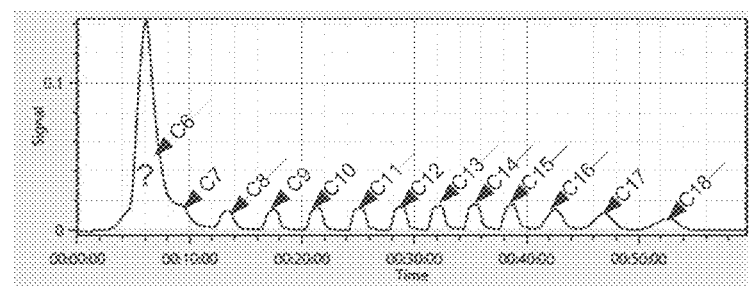
FIG. 5 is a chromatogram of a C6 through C18 carbon ladder with a methanol solvent showing the C6 peak being entirely and C6 peak being partially obscured by the solvent absorption.

The problem is reflected by the chromatograph of FIG. 5 (C6 through C18) where the peak identifying C6 is completely obscured and the peak identifying C7 is partially obscured by the solvent.

Figure 6:
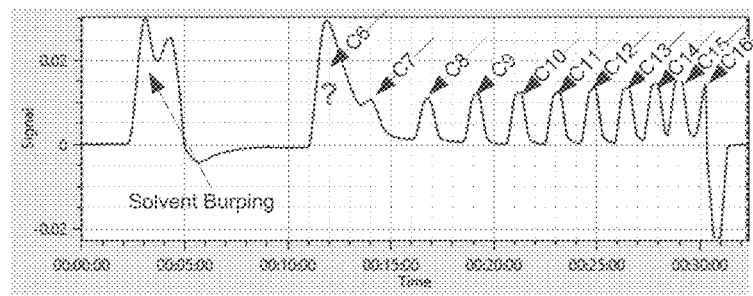
FIG. 6 is a chromatogram of a carbon ladder showing the effects of solvent burping and premature termination of the data collecting run.

An even more dramatic situation is presented in FIG. 6, where the early peaks in the run are caused by an uneven solvent behavior, what may be thought of as the solvent "burping" through the column, for example, making it hard to determine which peaks are caused by the solvent and which correspond to the carbon ladder. Another pitfall is the early termination of data collection based on an incorrect determination or "belief" that all hydrocarbons in the set had eluted through the column when in fact the run did not contain the complete carbon ladder. Therefore, based on the initial results obtained, it cannot be unambiguously assumed that the data gathered will contain the complete carbon ladder.

One solution addressing problems such as these is to remove the effects of the solvent by subtracting the solvent features from the sample spectrum before computing the chromatogram. This can be accomplished by determining a regression of the reference spectrum for solvent, methanol in this case, against the sample spectrum to determine the concentration of the solvent. The solvent spectrum is then multiplied by the regression scaling factor and subtracted from the sample spectrum before using the latter to compute the chromatograph. In other words:

Spectrum used in Chromatograph=Original Sample Spectrum−Solvent Spectrum*Regression Scale Factor In practice, this can be carried out in an automated manner, using, for example, a regression engine executing on the computer system 34, which allows a different curve definition for different concentrations in the reference spectrum. Such a multi-curve structure is advantageous since the spectrum for a vapor or gas can display shape modifications as the concentration of the vapor or gas changes. Since these shape changes can be non-linear across the spectrum, expressing them as a simple scaling of some base curve fails to capture or address these intricacies.

Figure 7:
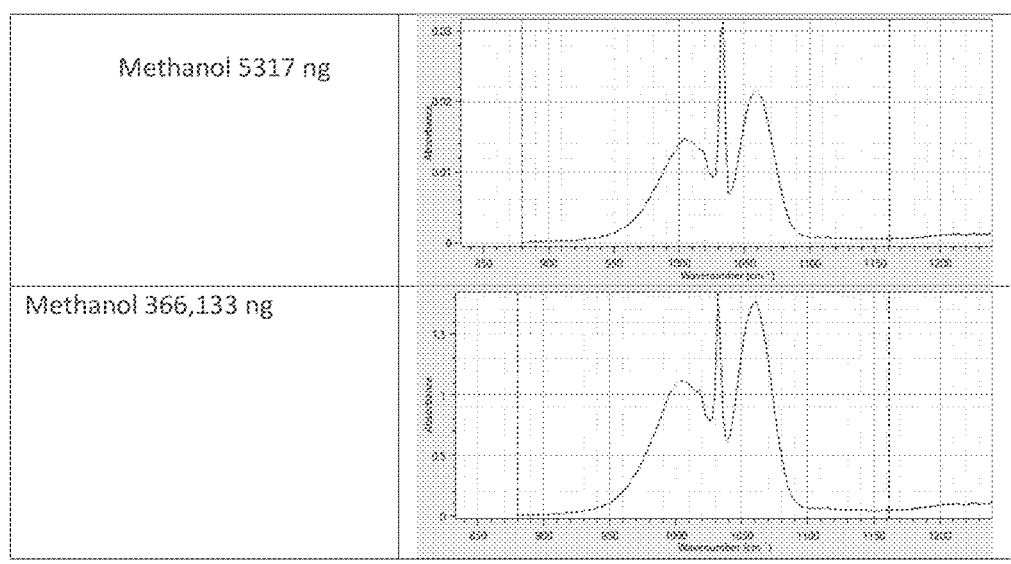
FIG. 7 are plots of absorbance as a function of wavenumber showing the absorbance spectra of methanol at two different concentrations.

An illustration is presented in FIG. 7, showing a region of the FTIR spectrum used for quantification, also referred to herein as the "quant" region, at two different methanol concentrations. The two spectra show that the height of the largest peak or Q-band or fundamental vibrational frequency at about 1033 $cm^{-1}$ relative to the neighboring smaller P-vibrational rotational band (to lower frequency) and R-vibrational rotational band to higher frequency changes with the change in concentration.

Figure 8:
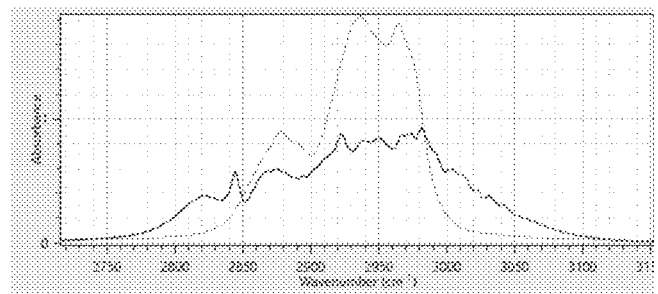
FIG. 8 is a plot of absorbance as a function of wavenumber showing the absorption spectra of hexane (gray) and methanol (black) and identifies the quant region of methanol, which lies above 3000 $cm^{-1}$ (red).

Shown in FIG. 8 are the IR absorption spectrum of C6 in gray and that of methanol (black plot). Choosing the methanol quant region between 3000 $cm^{-1}$ and 3150 $cm^{-1}$ avoids significant overlap with the hexane spectral features. This approach can be used to quantify methanol without having to include any of the hydrocarbons as interferences in the regression matrix. In a more general case, if the quant region of the solvent were to overlap with that of the carbon ladder, then the hydrocarbons would have to be added as interferences in the regression matrix.

Figure 9:
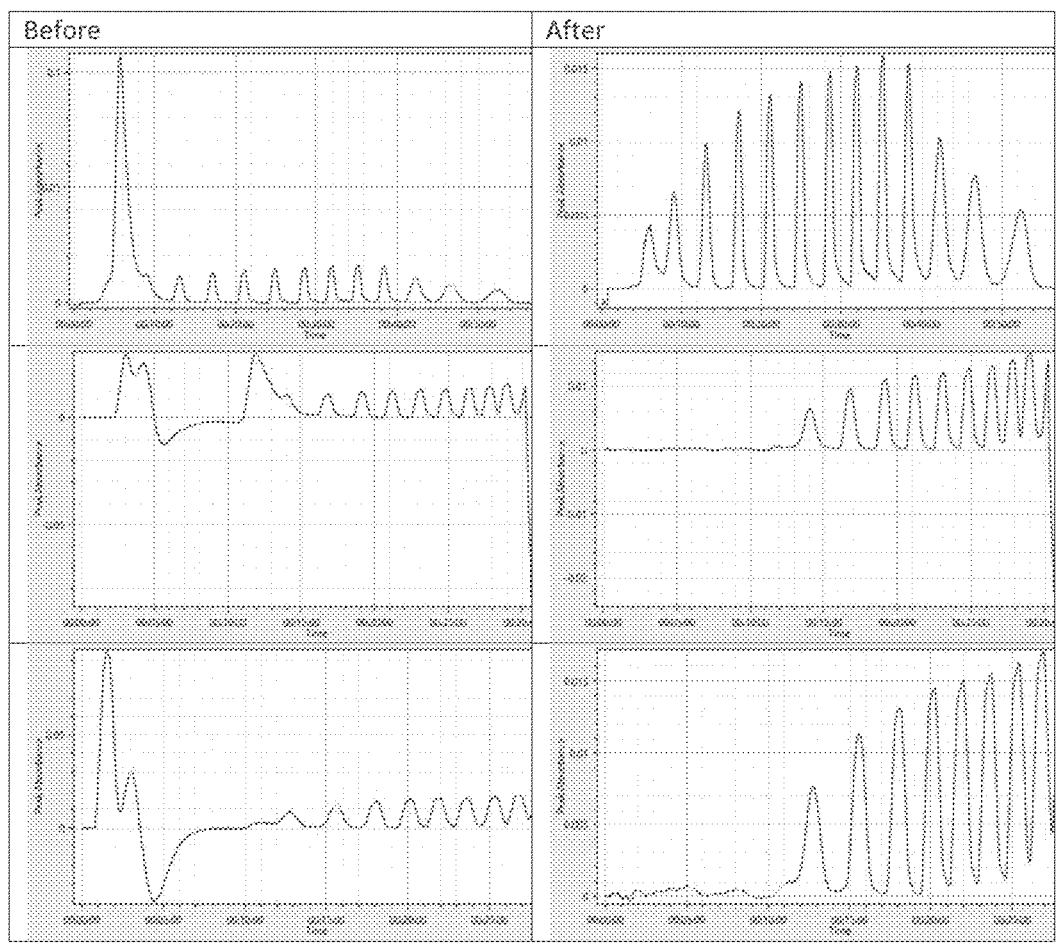
FIG. 9 is a series of chromatographs showing the effects of solvent correction (right-hand side) in comparison to the uncorrected data (left-hand side).

The graphs in FIG. 9 show the before (left hand side) and after (right hand side) effects of solvent corrections being applied to the chromatographs.

Figure 10:
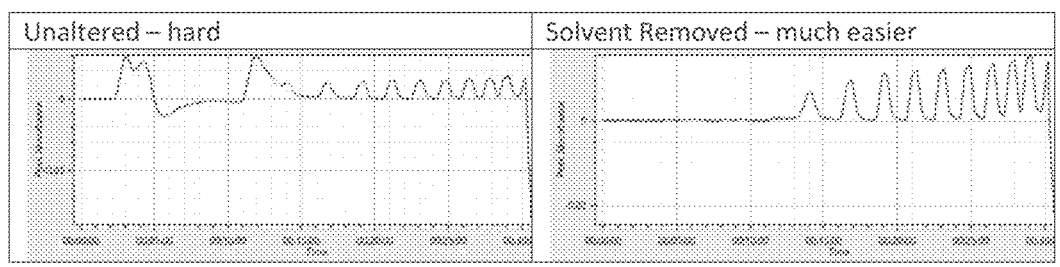
FIG. 10 compares chromatograms of the unaltered data (left) with data from which solvent effects were removed (right).

Although techniques for determining local maxima (peaks) are known and, in fact, have existed for decades, without the solvent removal approaches described herein, knowing which peaks in the graph are hydrocarbon peaks and which are solvent peaks would be very problematic. An illustration is provided in FIG. 10.

Some situations arise, however, when solvent removal approaches are not sufficient in peak recovery. Since the operator may not be aware of the existence of peaks that are obscured or 'lost", collection of data can be terminated prematurely. In the case discussed above, for instance, the C6 peak was not recovered and data collection was cut at C16.

Described below are some approaches for addressing problems raised by peaks that remain unrecoverable even after solvent effects have been addressed. These approaches also can be applied to cases in which solvent interference is not of concern. For example, situations may arise when one or more compounds in the carbon ladder may remain undetected for reasons other than solvent overlap, instances in which accounting for all compounds present in the calibration sample may be uncertain, and so forth.

Figure 11:
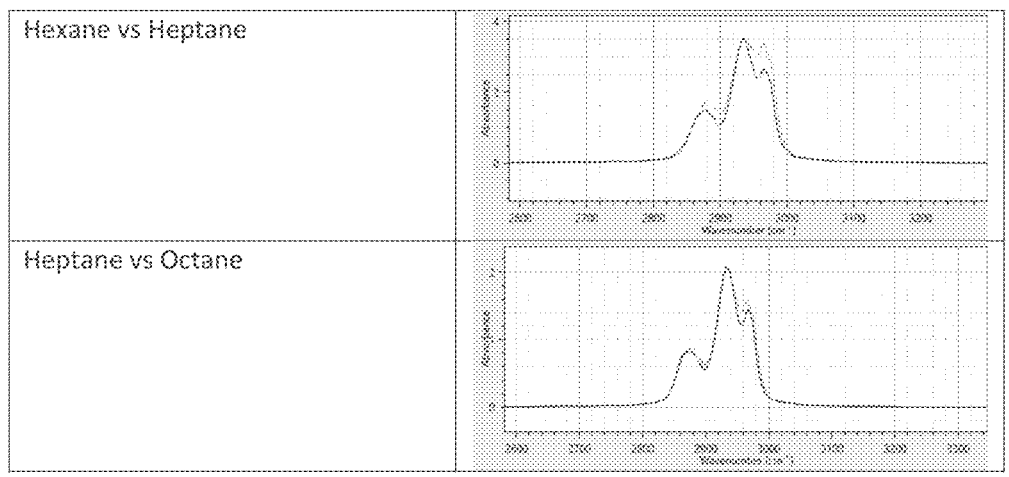
FIG. 11 is a plot of absorbance as a function of wavenumber illustrating the differences between the spectral fingerprint of hexane vs. heptane and heptane vs. octane.
Figure 12:
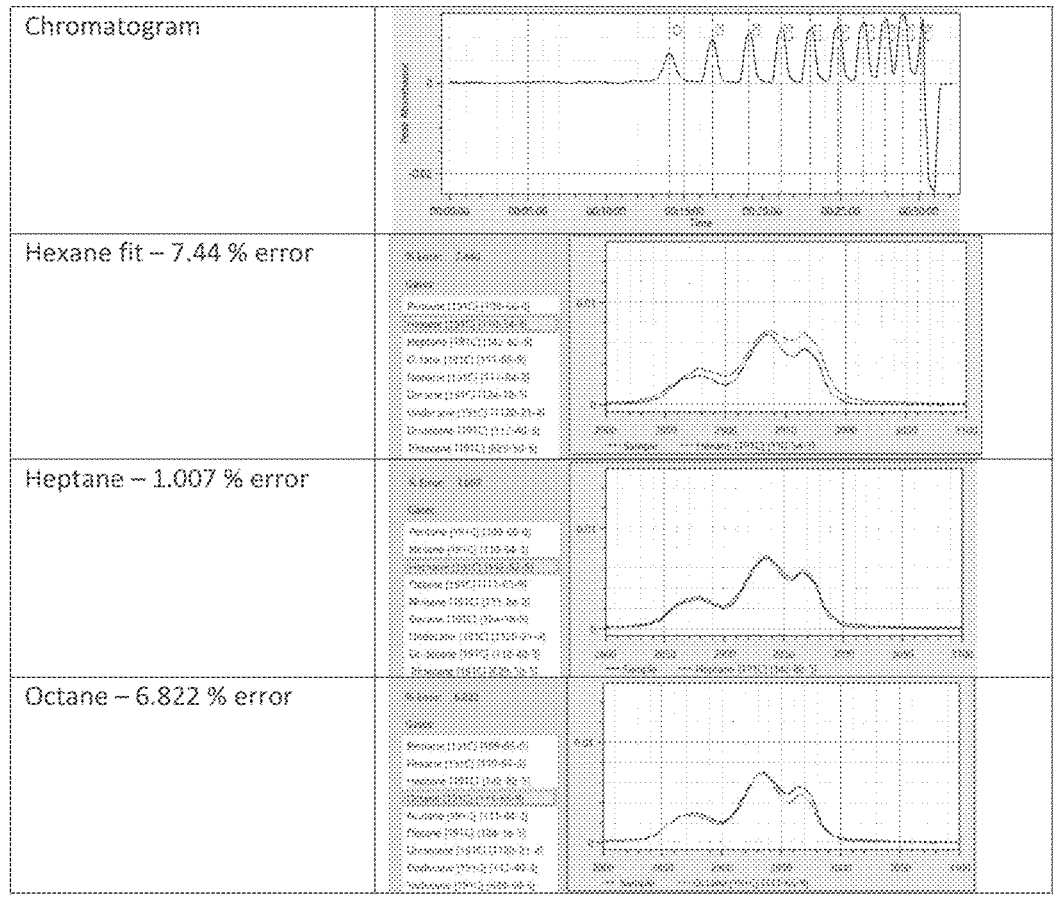
FIG. 12 is a series of fits of the reference spectrum of hexane, heptane and octane over a solvent corrected sample (target) spectrum and the error percentage observed in each case.

While it well established that the reference spectra for hydrocarbons are very similar, it is also true that measurable differences exist, even in the CH bands. This is shown for hexane (light gray) vs. heptane (dark gray) in the upper plot of FIG. 11 and heptane (light gray) vs octane (dark gray) in the lower plot of FIG. 11. In one embodiment described herein, the computer system 34 performs an evaluation of the "fit" of a hydrocarbon reference spectrum (available in a database that can be part of or accessible by computer 34) and a target (unknown) chromatogram peak. These curve fitting operations compare the reference spectrum against the solvent corrected sample (target) spectrum. An example of these metrics is shown in FIG. 12 and involves the C7 (heptane) absorption feature. As seen in this figure, an attempted fit between the observed sample feature and the C6 reference spectrum, C7 reference spectrum and C8 reference spectrum gave an error of 7.44%, 1.007% and 6.822%, respectively. The best fit (least error) identified the sample spectral feature as that of C7. Once one assignment is made (C7 in this example) the process can be repeated for one, more or all alkanes in the carbon ladder.

In many cases, what is generated (by an appropriate computational software, for example) is an aggregate metric for a hydrocarbon peak assignment. A suitable parameter that can be used to obtain a best match between the observed and reference spectra is the average error for the superimposed carbon ladder over the chromatograph peaks. Other types of fit metrics can be used instead of average error to give the same results. Examples include but are not limited to the average goodness of fit, or total error.

Further measures can be taken to expand the individualized identification of a member in the carbon ladder. For example, beyond optimizing the fit of any given alkane (least error between the reference and the sample spectral feature), establishing the order of peak assignments in the carbon ladder constrains the results in a manner that ensures that elution occurs in the proper sequence. As an example, C6 should never occur in time before C5 and the algorithm used can be designed to guarantee the appropriate sequence, Respecting the ordering of retention times (indices) in the peak assignment process prevents results in which a given elution occurs out of turn.

Figure 13:
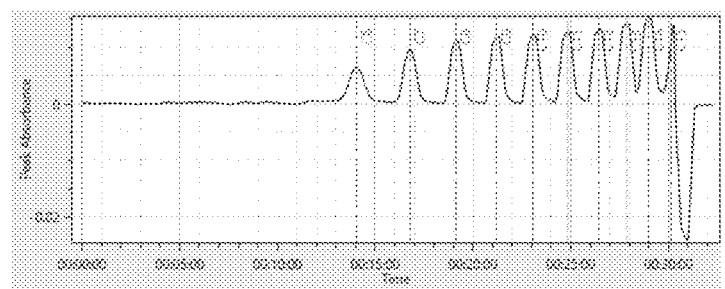
FIG. 13 is a chromatograph of a sample carbon ladder in which the members elute in the appropriate sequence and in which all the members between C6 and C15 are included (i.e., for this set, the ladder contains no gaps).

Mapping the chromatograph peaks in the carbon ladder by the computer system 34 can also be constrained to be continuous, in other words to encompass all hydrocarbons over a certain range sequentially. In some cases, some of the beginning and/or ending carbon numbers are allowed to be missing. In others, the "no gap" constraint can be loosened to allow some gaps within middle carbon numbers. An example of a C6 through C15 eluting in order and with no gaps over an elution period of about 30 minutes is shown in FIG. 13.

Once a calibration candidate is established, the final carbon ladder calibration can be generated by shifting the carbon ladder (obtained according to some or all of the processes described above) by one or more carbon numbers forward and/or backwards across the peaks, moving the entire ladder one peak at a time. An error metric is computed for each of these arrangements by the computer system 34 and the carbon ladder position that produces an overall best match, e.g., the smallest average error, is then used by the computer system 34. It is this shifting of the carbon ladder that allows the algorithm to handle undetected hydrocarbons peaks that may occur at the beginning of the run.

Figure 14:
FIG. 14 depicts a starting arrangement, its shift forward by one peak, its shift forward by two peaks and the corresponding fit (or error) used to pin down the correct carbon ladder arrangement.

An illustration is presented in FIG. 14. As seen in this figure, the starting chromatograph has an average error of 5.1. A one-peak shift forwards results in an average error of 1.3 (which corresponds to the best fit), while a two-peak forward shift results in an increase in the average error (to 6.3).

In many implementations, the reference spectrum is composed of a smaller set of hydrocarbons than the complete list that is used conventionally. It was discovered that only those carbon numbers that have a reference spectrum need to be included for a successful assignment of peaks. In one example, the method is conducted successfully with only 12 hydrocarbons, C5 through C16.

Similar calibrations can be generated using Lee indices (including, for example, naphthalene (RI=200), phenanthrene (RI=300), chrysene=400), picene or benzo(g, h,i)perylene (RI=500), etc.) or other sets of compounds.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for generating a carbon ladder calibration chromatogram, the process comprising:
    generating an initial chromatogram of a sample eluting through a gas chromatography (GC) column, wherein the sample comprises carbon ladder compounds;
    comparing a spectrum of one or more observed peaks in the initial chromatogram with reference spectra of the compounds;
    assigning the one or more observed peaks by determining a best match between the spectrum of the one or more observed peak and the reference spectra to obtain a candidate calibration chromatograph; and
    shifting the candidate calibration chromatogram by one or more carbon numbers to determine an overall best match, thereby generating the carbon ladder calibration chromatogram; and
    wherein solvent effects are reduced by:
    obtaining a regression of the reference spectrum for a solvent against a sample spectrum in a selected spectral region, to determine a solvent concentration; and
    subtracting from the sample spectrum the product obtained by multiplying a solvent spectrum by a regression scaling factor.

2. The calibration process of claim 1, wherein the observed peaks are detected by optical spectroscopy.

3. The calibration process of claim 1, wherein the observed peaks are detected by Fourier transform infrared (FTIR) spectrometry.

4. The calibration process of claim 1, wherein the initial chromatogram is corrected by removing solvent effects.

5. The process of claim 1, wherein the selected spectral region is a region devoid of features characterizing the carbon ladder compounds.

6. The process of claim 1, wherein the process is conducted under a no gap constraint.

7. The process of claim 1, wherein the process is conducted by following a normal elution order of the carbon ladder compounds.

8. The process of claim 1, wherein the process allows for a gap in the carbon ladder.

9. The process of claim 1, wherein the candidate calibration chromatograph is shifted by one or more carbon numbers forward and/or backwards across the peaks, moving the entire ladder one peak at a time.

10. The process of claim 1, wherein the carbon ladder compounds include hydrocarbons.

11. The process of claim 1, wherein retention indices of the carbon ladder compounds are Kovats indices.

12. The process of claim 1, wherein retention indices of the carbon ladder compounds used are Lee indices.

13. The process of claim 1, wherein the best match or the overall best match is expressed by a best fit, least error, least average error or least total error.

14. The process of claim 1, wherein the sample eluted from the GC column is temporally resolved into components that are directed to a sample cell and detected by Fourier transform infrared (FTIR) spectrometry.

15. The process of claim 14, wherein the sample cell is a multiple path cell.

* * * * *